(12) United States Patent
Pilkington (10) Patent No.: US 11,642,472 B2
(45) Date of Patent: May 9, 2023

(54) HUB FOR COUPLING A CANNULA WITH A TRANSFER DEVICE

(71) Applicant: Black Tie Medical Inc., San Diego, CA (US)

(72) Inventor: Kyle M. Pilkington, San Diego, CA (US)

( * ) Notice: Subject to any disclaimer, the term of this patent is extended or adjusted under 35 U.S.C. 154(b) by 308 days.

(21) Appl. No.: 17/003,862

(22) Filed: Aug. 26, 2020

(65) Prior Publication Data

US 2021/0060266 A1    Mar. 4, 2021

Related U.S. Application Data

(60) Provisional application No. 62/892,530, filed on Aug. 27, 2019.

(51) Int. Cl.
| | | |
|---|---|---|
| *A61M 5/32* | (2006.01) | |
| *A61M 5/315* | (2006.01) | |
| *A61M 5/34* | (2006.01) | |
| *A61M 25/00* | (2006.01) | |
| *A61M 5/31* | (2006.01) | |
| *A61M 39/10* | (2006.01) | |

(52) U.S. Cl.
CPC ...... *A61M 5/3293* (2013.01); *A61M 5/31565* (2013.01); *A61M 5/347* (2013.01); *A61M 25/0097* (2013.01); *A61M 5/3129* (2013.01); *A61M 2039/1033* (2013.01); *A61M 2039/1038* (2013.01)

(58) Field of Classification Search
CPC ............... A61M 5/3293; A61M 5/347; A61M 5/31565; A61M 5/3129; A61M 2039/1083; A61M 2039/1088; A61M 5/344; A61M 2039/1033; A61M 2039/1038; A61M 25/0097; F16B 25/0052; F16B 33/02
See application file for complete search history.

(56) References Cited

U.S. PATENT DOCUMENTS

| | | |
|---|---|---|
| 4,931,040 A | 6/1990 | Haber et al. |
| 4,950,241 A | 8/1990 | Ranford |
| 5,002,538 A | 3/1991 | Johnson |
| 5,017,191 A | 5/1991 | Yamada et al. |
| 5,176,662 A | 1/1993 | Bartholomew et al. |
| 5,236,356 A | 8/1993 | Davis et al. |

(Continued)

FOREIGN PATENT DOCUMENTS

ES    2843824 T3 * 7/2021    ............ A61B 17/164

*Primary Examiner* — Katherine H Schwiker
*Assistant Examiner* — Robert F Allen
(74) *Attorney, Agent, or Firm* — Rodney F. Brown (57) ABSTRACT

A cannula hub includes a shaft mount segment and a cannula coupling segment. A set of coupling nubbins radially extend from the outer surface of the cannula coupling segment. The coupling nubbins are aligned with one another along a helical cannula coupling pathway on the outer surface and are adapted to be received within a cooperative helical groove on a transfer vessel. The coupling nubbins have a protrusion projection distance that is greater than the depth of the groove. When a sufficient rotational force is applied to the cannula hub, the coupling nubbins score the inside face of the groove which increases the groove depth and enables the coupling nubbins to advance along the groove while forming a tight compression fit of the coupling nubbins within the groove.

18 Claims, 9 Drawing Sheets

(56) References Cited

U.S. PATENT DOCUMENTS

| | | | |
|---|---|---|---|
| 5,312,362 A | 5/1994 | Pfolsgraf et al. | |
| 5,454,409 A | 10/1995 | McAffer et al. | |
| 5,462,534 A | 10/1995 | Debreczeni | |
| 5,489,205 A | 2/1996 | Davis et al. | |
| 5,609,584 A | 3/1997 | Gettig et al. | |
| 6,217,269 B1 * | 4/2001 | Jentzen | F16B 41/005 411/949 |
| 6,423,036 B1 | 7/2002 | Van Huizen | |
| 6,569,118 B2 | 5/2003 | Johnson et al. | |
| 6,955,660 B2 | 10/2005 | Fisher | |
| 7,942,854 B1 | 5/2011 | Von Oepen et al. | |
| 7,967,786 B2 | 6/2011 | Westrate | |
| 8,029,476 B2 | 10/2011 | Rosenberg et al. | |
| 8,172,803 B2 | 5/2012 | Morrissey et al. | |
| 8,226,614 B2 | 7/2012 | Turner et al. | |
| RE43,597 E | 8/2012 | Johnson et al. | |
| 8,292,851 B2 | 10/2012 | Ferrari | |
| 8,597,241 B2 | 12/2013 | Yang et al. | |
| 8,814,833 B2 | 8/2014 | Farrell et al. | |
| 10,702,629 B2 | 7/2020 | Pilkington et al. | |
| 2008/0188816 A1 * | 8/2008 | Shimazaki | A61M 5/34 604/240 |
| 2014/0339811 A1 * | 11/2014 | Wong | A61M 39/1011 29/525.02 |
| 2015/0119863 A1 * | 4/2015 | Christensen | A61M 39/10 604/539 |
| 2019/0275314 A1 * | 9/2019 | Jeffrey | A61M 39/20 |

* cited by examiner

FIG. 10

HUB FOR COUPLING A CANNULA WITH A TRANSFER DEVICE

BACKGROUND OF THE INVENTION

The present invention relates generally to medical devices, and more particularly to cannulas.

A cannula is a tubular conduit used in medical procedures that enables transfer of material between a transfer vessel and a patient's body when one end of the cannula penetrates the patient's skin and the other end of the cannula is coupled with the transfer vessel. A syringe is one type of transfer vessel that can be coupled with a cannula for various medical applications. U.S. patent Ser. No. 10/702,629, which is incorporated herein by reference, shows an exemplary syringe in FIGS. 2 and 3 thereof. Conventional syringes have a barrel and a plunger that are typically fabricated from a rigid plastic that is transparent or translucent. The barrel is an open-ended tube with a cylindrical, hollow, elongate configuration that encircles a barrel chamber. One open end of the barrel has the same relatively wide diameter as the barrel chamber. The other end of the barrel tapers to an open tip that is coupleable with a cannula and has a much narrower diameter than the barrel chamber.

The wider open end of the barrel receives an internal end of the plunger therethrough into the barrel chamber while the opposite external end of the plunger remains outside of the barrel chamber. Material is drawn into the barrel chamber via the barrel tip and cannula which is coupled therewith when the plunger is displaced away from them in the manner of a piston and material is expelled from the barrel chamber via the barrel tip and cannula when the plunger is displaced toward them.

It is apparent that secure coupling of the barrel tip with the cannula is required for effective operation of the syringe. As such, barrel tips and cannulas are specifically configured to facilitate secure coupling with one another. U.S. Pat. No. RE43597, which is incorporated herein by reference, discloses a cannula and a barrel tip that are cooperatively configured for secure coupling with one another. The barrel tip has a pair of coaxial tubes, wherein the inside tube is nested within the outside tube and an annular recess if formed between them. The inside tube is an open port into the barrel chamber and the outside tube is a Luer connector having an internal thread formed on the inner surface of the outside tube facing the annular recess. The barrel tip disclosed in U.S. patent Ser. No. 10/702,629 has a similar configuration.

Certain medical procedures require a practitioner to manipulate the cannula in an aggressive and forceful manner while it is attached to the syringe or some other transfer vessel to achieve a desired outcome. For example, when using a cannula coupled with a transfer vessel to harvest fat from one location in the body of a patient and re-deposit the harvested fat at another location in the body, the practitioner may be required to forcefully manipulate the cannula in any number of directions after it penetrates the skin, e.g., twisting, back and forth, side to side and/or up and down, to overcome the resistance of the body. Other medical procedures which may require a practitioner to aggressively and/or forcefully manipulate the cannula include bone marrow injection and PRP (platelet-rich plasma) injection. In such cases manipulation of the cannula can subject the coupling between the cannula and transfer vessel to undue multidirectional linear and/or rotational forces which can undesirably loosen the coupling or even cause complete uncoupling of the cannula and transfer vessel termed self-release, particularly when the coupling is lubricated by fat or other body fluids coming into contact with it. As such a need exists for a cannula that resists loosening or self-release from a transfer vessel with which it is coupled during the course of the medical procedure. Therefore, it is inter alia an object of the present invention to satisfy this need. This object and others are accomplished in accordance with the invention which will be understood from the drawings and the following detailed description.

SUMMARY OF THE INVENTION

The present invention may be characterized as a cannula hub having a shaft mount segment and a cannula coupling segment. The shaft mount segment is adapted to mount a shaft thereon. The cannula coupling segment has a tubular configuration with a base, an upper hub end and an outer surface. A set of coupling nubbins radially extend from the outer surface of the cannula coupling segment. The set of coupling nubbins includes a first coupling nubbin and a second coupling nubbin aligned with, but spaced apart from one another along a helical cannula coupling pathway on the outer surface. The first coupling nubbin is preferably positioned more proximal the base along the cannula coupling pathway than the second coupling nubbin of the set. The first and second coupling nubbins of the set are adapted to be received within a cooperative first helical groove on a transfer vessel. The first helical groove has a first groove depth and the first coupling nubbin of the set has a protrusion projection distance that is greater than the first groove depth. The second coupling nubbin of the set has a protrusion projection distance that is greater than the protrusion projection distance of the first coupling nubbin.

In accordance with one embodiment, the cannula hub further comprises a helical coupling alignment guide radially extending from the outer surface and following the cannula coupling pathway around the outer surface. The coupling alignment guide preferably has a start point positioned more proximal the base along the cannula coupling pathway than the first and second coupling nubbins of the set, an arc length of about 90° and a protrusion projection distance less than the protrusion projection distance of the first coupling nubbin of the set.

In accordance with another embodiment, the set of coupling nubbins further includes a third coupling nubbin and a fourth coupling nubbin aligned with the first and second coupling nubbins of the set along the cannula coupling pathway. The third coupling nubbin is positioned between the first and second coupling nubbins of the set and the fourth coupling nubbin is positioned after the second coupling nubbin of the set on the cannula coupling pathway such that each successive coupling nubbin on the cannula coupling pathway is separated from its immediately preceding coupling nubbin on the cannula coupling pathway by a separation distance. The separation distance preferably has an arc length of about 90° on the cannula coupling pathway. The third coupling nubbin preferably has a projection protrusion distance equal to the projection protrusion distance of the first coupling nubbin of the set and the fourth coupling nubbin preferably has a projection protrusion distance equal to the projection protrusion distance of the second coupling nubbin of the set.

In accordance with yet another embodiment, the cannula coupling pathway on the outer surface is a first cannula coupling pathway and the set of coupling nubbins is a first set of coupling nubbins. The cannula hub further comprises a second set of coupling nubbins including a first coupling nubbin and a second coupling nubbin. The first and second coupling nubbins of the second set are aligned with, but are spaced apart from one another along a second helical cannula coupling pathway on the outer surface. The first and second coupling nubbins of the second set are adapted to be received within a cooperative second helical groove with a second groove depth on the transfer vessel. The first coupling nubbin of the second set has a protrusion projection distance that is greater than the second groove depth and the second coupling nubbin of the second set has a protrusion projection distance that is greater than the protrusion projection distance of the first coupling nubbin of the second set.

The present invention may be alternately characterized as a cannula hub having a shaft mount segment and a cannula coupling segment, but with two sets of coupling nubbins radially extend from the outer surface of the cannula coupling segment. The first set of coupling nubbins includes a first coupling nubbin and a second coupling nubbin aligned with, but spaced apart from one another along a first helical cannula coupling pathway on the outer surface. The first and second coupling nubbins of the first set are adapted to be received within a cooperative first helical groove with a first groove depth on a transfer vessel. The first coupling nubbin of the first set has a protrusion projection distance that is greater than the first groove depth and the second coupling nubbin of the first set has a protrusion projection distance that is greater than the protrusion projection distance of the first coupling nubbin of the first set.

The second set of coupling nubbins includes a first coupling nubbin and a second coupling nubbin aligned with, but spaced apart from one another along a second helical cannula coupling pathway on the outer surface. The first and second coupling nubbins of the second set are adapted to be received within a cooperative second helical groove with a second groove depth on a transfer vessel. The first coupling nubbin of the second set has a protrusion projection distance that is greater than the second groove depth and the second coupling nubbin of the second set has a protrusion projection distance that is greater than the protrusion projection distance of the first coupling nubbin of the second set. The protrusion projection distance of the first coupling nubbin of the first set is preferably equal to the protrusion projection distance of the first coupling nubbin of the second set, the protrusion projection distance of the second coupling nubbin of the first set is preferably equal to the protrusion projection distance of the second coupling nubbin of the second set and the first groove depth is preferably equal to the second groove depth.

In accordance with one embodiment, the cannula hub further comprises a first helical coupling alignment guide radially extending from the outer surface and following the first cannula coupling pathway around the outer surface and a second helical coupling alignment guide radially extending from the outer surface and following the second cannula coupling pathway around the outer surface. The first coupling alignment guide preferably has a first start point positioned more proximal the base along the first cannula coupling pathway than the first coupling nubbin and second coupling nubbin of the first set. The second coupling alignment guide preferably has a second start point positioned more proximal the base along the second cannula coupling pathway than the first coupling nubbin and second coupling nubbin of the second set. The first start point and the second start point are preferably positioned on the outer surface at opposite sides of the base 180° apart from one another and the first and second coupling alignment guide each preferably has an arc length of about 90°.

The present invention may be alternately characterized as a method for coupling a cannula hub with a transfer vessel. In accordance with an embodiment of the method, the practitioner engages a start point of a cooperative helical groove on a transfer vessel with a start point of a helical coupling alignment guide positioned along a helical cannula coupling pathway on an outer surface of a cannula coupling segment included in a cannula hub. The helical groove has an inside face defining a groove depth. The cannula hub is rotated to advance the coupling alignment guide along the helical groove past the start point of the helical groove, thereby engaging a coupling nubbin with the start point of the helical groove, wherein the coupling nubbin is aligned with the coupling alignment guide in the cannula coupling pathway and has a protrusion projection distance greater than the groove depth. A sufficient rotational force is applied to the cannula hub to score the inside face of the helical groove with the coupling nubbin, thereby increasing the groove depth and enabling the coupling nubbin to advance along the helical groove past the start point of the helical groove.

The present invention will be further understood from the drawings and the following detailed description.

BRIEF DESCRIPTION OF THE DRAWINGS

The below-listed drawing figures illustrate one or more embodiments of the present invention by way of example and not by way of limitation. Common reference characters may be used among the different drawing figures to indicate the same or similar structural elements.

DETAILED DESCRIPTION OF PREFERRED EMBODIMENTS

Figure 1:
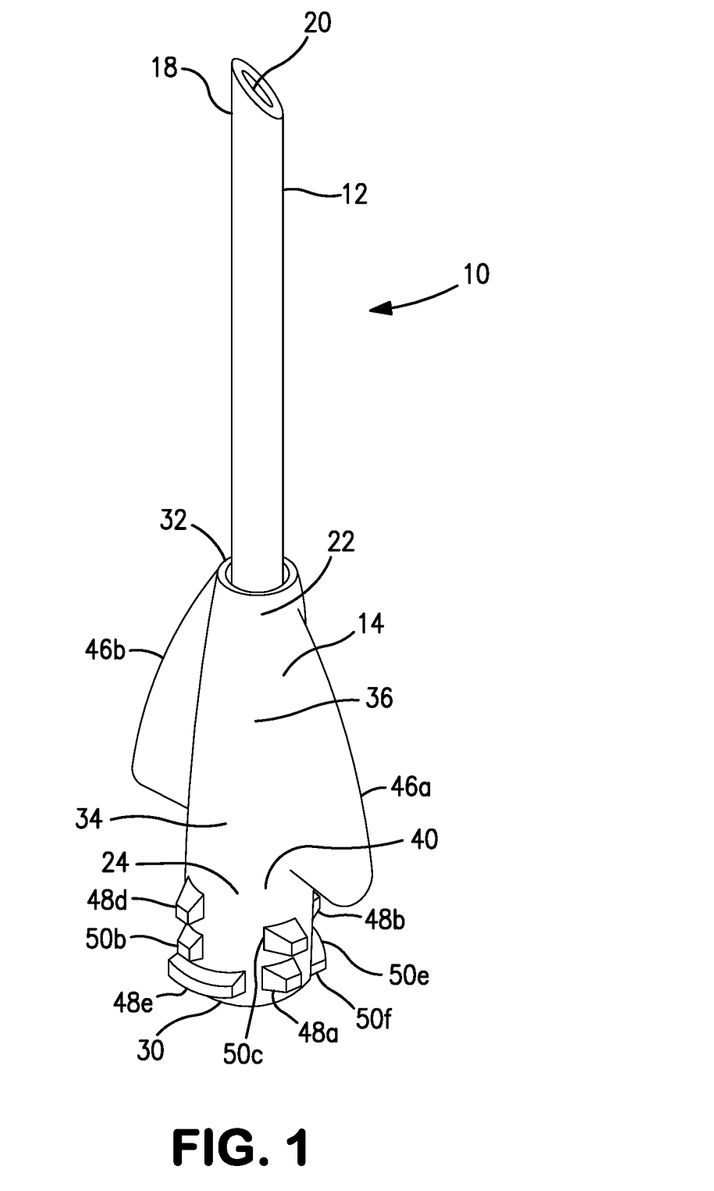
FIG. 1 is a perspective view of an embodiment of a cannula.

An embodiment of a cannula generally designated 10 is shown in FIG. 1. The cannula 10 comprises a shaft 12 and a hub 14. The cannula shaft 12 is configured to penetrate the skin of a patient and temporarily reside in the patient's body within or below the skin during the performance of a desired medical procedure. The cannula hub 14 is configured to securely couple the cannula 10 with a transfer vessel during the medical procedure. There are a number of medical procedures for which the cannula 10 has utility including cosmetic and plastic surgical procedures and regenerative medicine procedures. The cannula 10 has particular utility for fat transfer procedures which encompass fat harvesting and fat re-injection. Additional medical procedures for which the cannula 10 has utility include the injection of bone marrow and blood components such as PRP (platelet-rich plasma).

The cannula shaft 12 and hub 14 are preferably sterile and disposable so that the cannula 10 is amenable to single-use applications. The materials of construction for the cannula shaft 12 and hub 14 are preferably biocompatible, rigid, fluid impervious and inert to fluids typically encountered during the medical procedures in which the cannula 10 is used. A preferred material of construction for the cannula shaft 12 is a relatively rigid metal. The material of construction for the cannula hub 14 is preferably harder than the material from which a cooperative coupler on a transfer vessel to be coupled with the cannula hub 14 is constructed. Exemplary materials of construction for the cannula hub 14 satisfying the above criteria include metals, hard plastics or composites. Relatively rigid hard plastics that can be molded, machined or otherwise fabricated into the configuration described herein are most preferred.

Positional or directional terms such as top and bottom, upper and lower, above and below, up and down, and the like are used herein to denote the relative position or movement of structures along the central longitudinal axis of the cannula hub 14. Positional or directional terms such as inner, inside, in, and the like are used herein to describe a structure facing or extending radially toward the central longitudinal axis of the cannula hub 14, while positional or directional terms such as outer, outside, out, and the like are used herein to describe a structure facing or extending radially away from the central longitudinal axis of the cannula hub 14.

Figure 4:
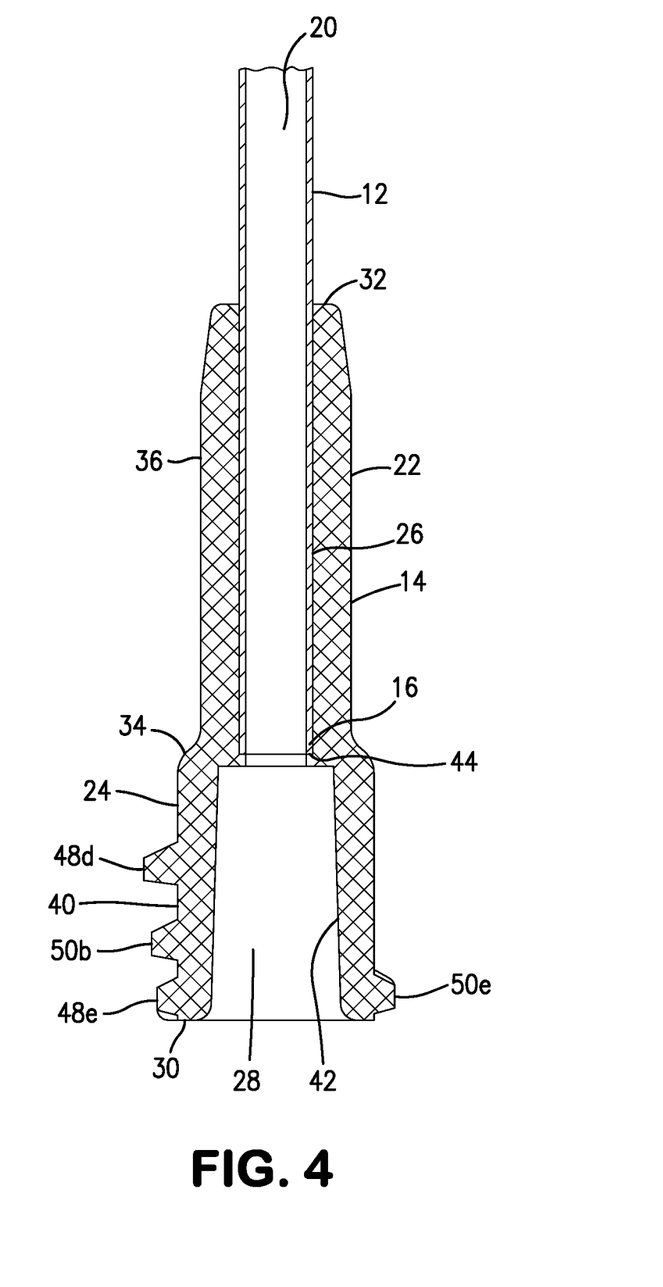
FIG. 4 is the same view of the cannula hub as FIG. 3, but additionally including a partial cross section of the shaft which is shown in the cannula of FIG. 1.
Figure 5:
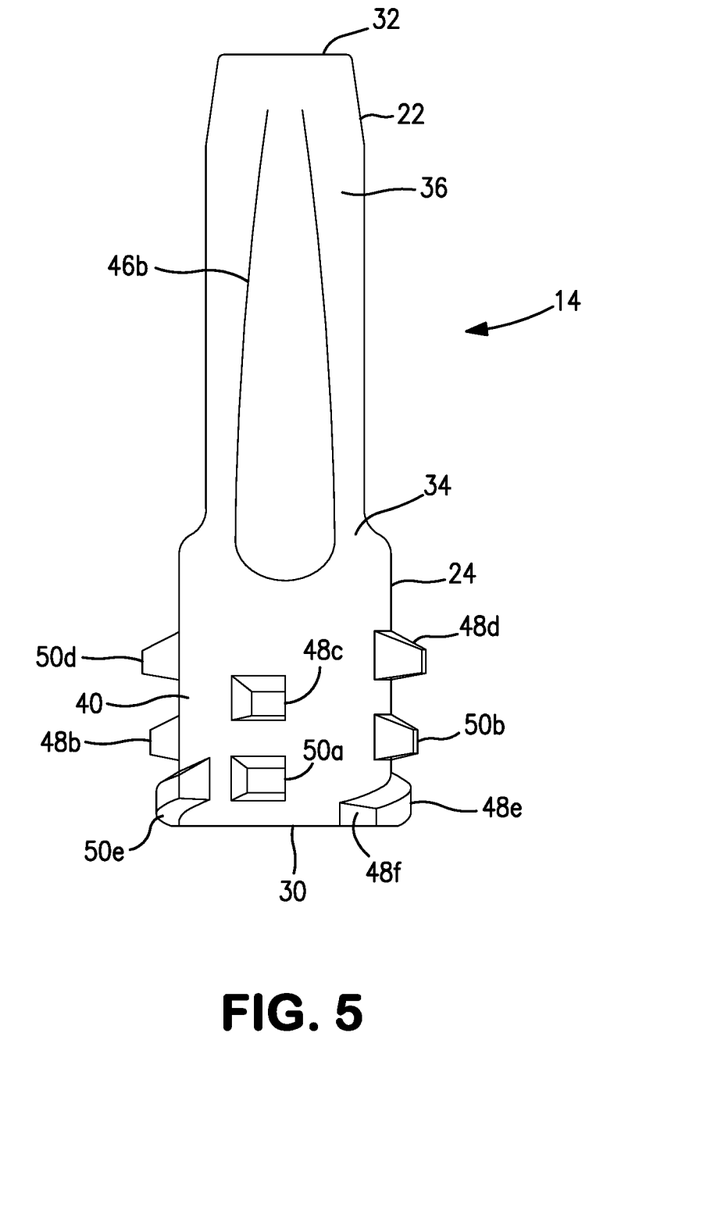
FIG. 5 is a side elevation view of the cannula hub of FIG. 2, but rotated 90° counterclockwise from the view of FIG. 2.
Figure 6:
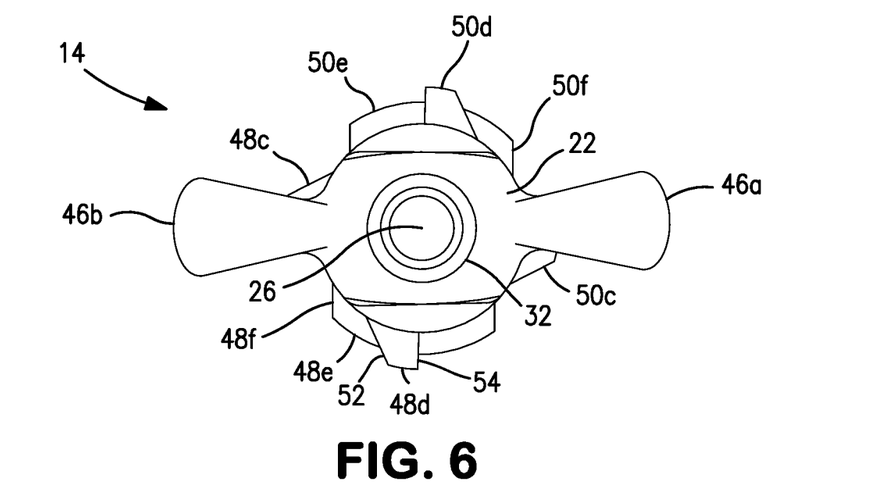
FIG. 6 is a top down view of the cannula hub of FIG. 2.
Figure 7:
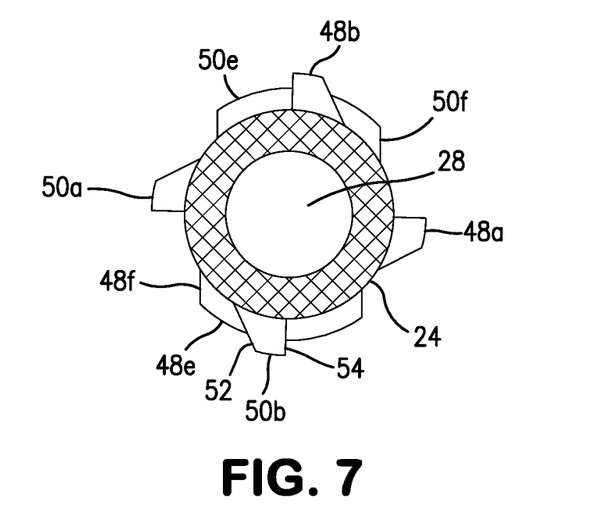
FIG. 7 is a cross section of the cannula hub of FIG. 2 taken along the section line 7-7.

With reference to FIGS. 1 and 4, the cannula shaft 12 has a narrow, elongate open-ended tubular configuration with a first shaft end 16 and an opposing second shaft end 18. The first shaft end 16 is a blunted end that is enclosed within and attached to the cannula hub 14 while the second shaft end 18 is a sharpened beveled tip that is fully exposed. As such, the first shaft end 16 is more proximal to the hub 14 than the second shaft end 18. The shaft 12 has a longitudinal shaft bore termed a lumen 20 that extends its entire length. The present embodiment of the cannula shaft 12 is often commonly termed a needle because its exposed end is a sharpened tip. Nevertheless, it is apparent to one of ordinary skill in the art that the present teaching applies to cannulas having alternately configured shafts and that such cannulas are within the scope of the present invention. Accordingly, the particular cannula shaft 12 is taught herein by way of example and not by way of limitation.

With additional reference to FIGS. 2, 3 and 5-7, the cannula hub 14 is a unitary structure having two contiguous segments, a shaft mount segment 22 and a cannula coupling segment 24, that are serially positioned end to end in alignment with the central longitudinal axis of the cannula hub 14. The contiguous segments 22, 24 in combination form an open-ended tube that is wider and shorter than the shaft 12. The cannula hub 14 has a longitudinal hub bore extending continuously through its entire length. The hub bore is segmented into a first hub bore segment 26 extending through the shaft mount segment 22 and a second hub bore segment 28 extending through the cannula coupling segment 24.

Figure 2:
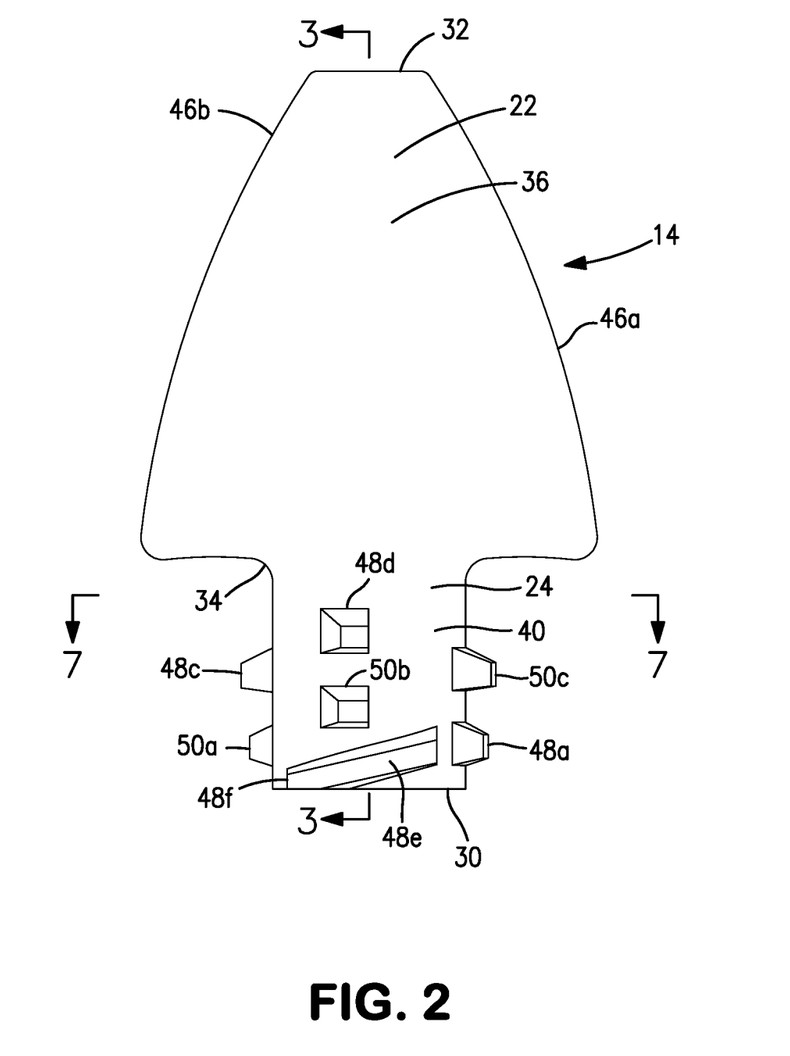
FIG. 2 is a side elevation view of the cannula hub which is shown in the cannula of FIG. 1.
Figure 3:
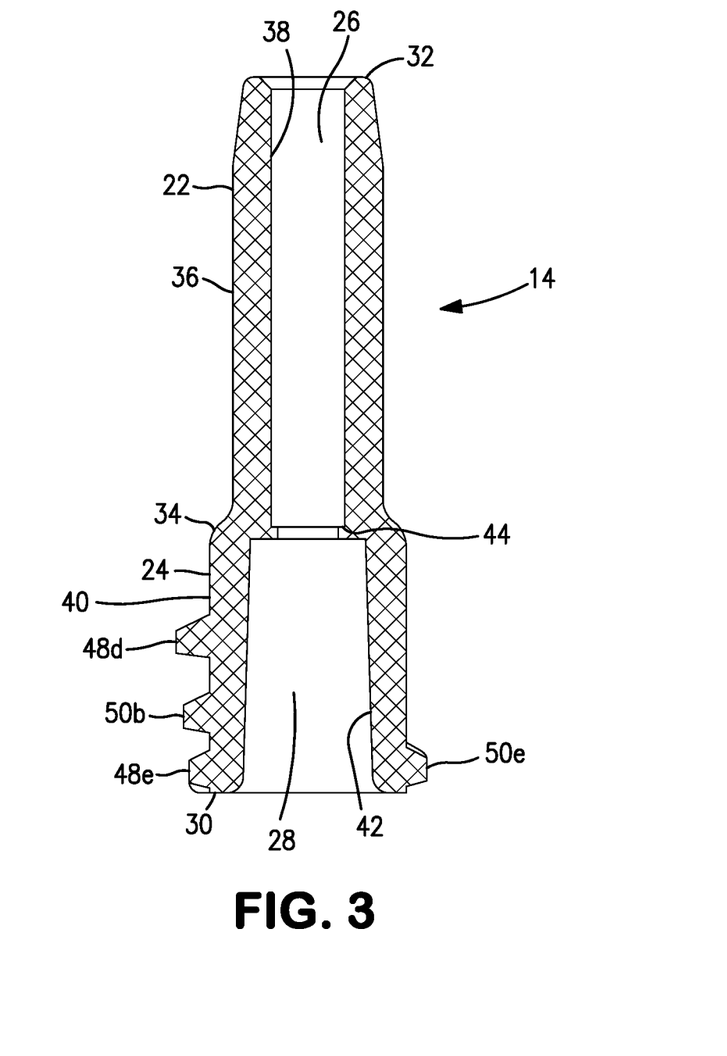
FIG. 3 is a cross section of the cannula hub of FIG. 2 taken along the section line 3-3.

The cannula hub 14 has a base 30 which is a first or lower hub end and corresponds to the open bottom end of the cannula coupling segment 24. The cannula hub 14 also has a second or upper hub end 32 that corresponds to the beveled open top end of the shaft mount segment 22. The upper hub end 32 is more proximal to the cannula shaft 12 than the base 30. The shaft mount segment 22 and cannula coupling segment 24 merge into one another at an intersection 34 about midway along the length of the cannula hub 14 between the base 30 and upper hub end 32. The intersection 34 corresponds to the bottom end of the shaft mount segment 22 and the top end of the cannula coupling segment 24.

The shaft mount segment 22 has an exposed outer surface 36 that defines the outside diameter of the shaft mount segment 22 and an inner surface 38 bounding the first hub bore segment 26 that defines the inside diameter of the shaft mount segment 22, alternately termed the diameter of the first hub bore segment 26. The cannula coupling segment 24 similarly has an exposed outer surface 40 that defines the outside diameter of the cannula coupling segment 24 and an inner surface 42 bounding the second hub bore segment 28 that defines the inside diameter of the cannula coupling segment 24, alternately termed the diameter of the second hub bore segment 28.

The cannula coupling segment 24 and the second hub bore segment 28 extending therethrough are generally wider and shorter than the shaft mount segment 22 and the first hub bore segment 26 extending therethrough, respectively. The diameter of the first hub bore segment 26 is constant along essentially its entire length, but the second hub bore segment 28 has a slight taper as it extends from the base 30 to the intersection 34. Regardless, the diameter of the second hub bore segment 28 is at all points thereon greater than the constant diameter of the first hub bore segment 26.

The diameter of the first hub bore segment 26 is specifically selected in correspondence with the outside diameter of the cannula shaft 12. In particular, the diameter of the first hub bore segment 26 is sized only slightly larger than the outside diameter of the cannula shaft 12 so that the first shaft end 16 fits snugly within the first hub bore segment 26. However, the diameter of the longitudinal hub bore is reduced at the intersection 34 so that it is slightly less than the diameter of the first hub bore segment 26, thereby creating a shoulder 44 in the longitudinal hub bore. When the cannula shaft 12 is positioned within the first hub bore segment 26 as shown in FIG. 4, the shoulder 44 acts as a stop for the first shaft end 16 which abuts up against the shoulder 44. The cannula shaft 12 is preferably permanently fixably attached to the inner surface 38 of the shaft mount segment 22 by securing means such as bonding, gluing, welding, combinations thereof, or the like. Attachment of the cannula shaft 12 to the cannula hub 14 is typically effected by the cannula manufacturer during the cannula manufacturing process.

The external profile of the shaft mount segment 22 has a taper as it extends upward from the intersection 34 to the upper hub end 32 which provides the shaft mount segment 22 with a substantially conical external profile. The taper is due to a decrease in the outside diameter of the shaft mount segment 22 from the intersection 34 to the upper hub end 32 as measured between points on opposite sides of the outer surface 36. A pair of identical essentially planar triangular-shaped protrusions 46a, 46b termed first and second wings, respectively, extend radially outward from the outer surface 36 of the shaft mount segment 22 on opposite sides thereof. The wings 46a, 46b function as fingerholds to facilitate manual cooperative coupling of the cannula hub 14 and a transfer vessel in a manner described below with reference to FIGS. 9 and 10.

The external profile of the cannula coupling segment 24 also has a taper as it extends upward from the base 30 to the intersection 34 due to a slight decrease in the outside diameter of the cannula coupling segment 24 from the base 30 to the intersection 34 as measured between points on opposite sides of the outer surface 40. However, the taper of the cannula coupling segment 24 is much less than the taper of the shaft mount segment 22. Therefore, the external profile of the cannula coupling segment 24 is substantially cylindrical rather than conical. In any case, the outside diameter of the cannula coupling segment 24 is at all points thereon greater than the outside diameter of the shaft mount segment 22.

Figure 8:
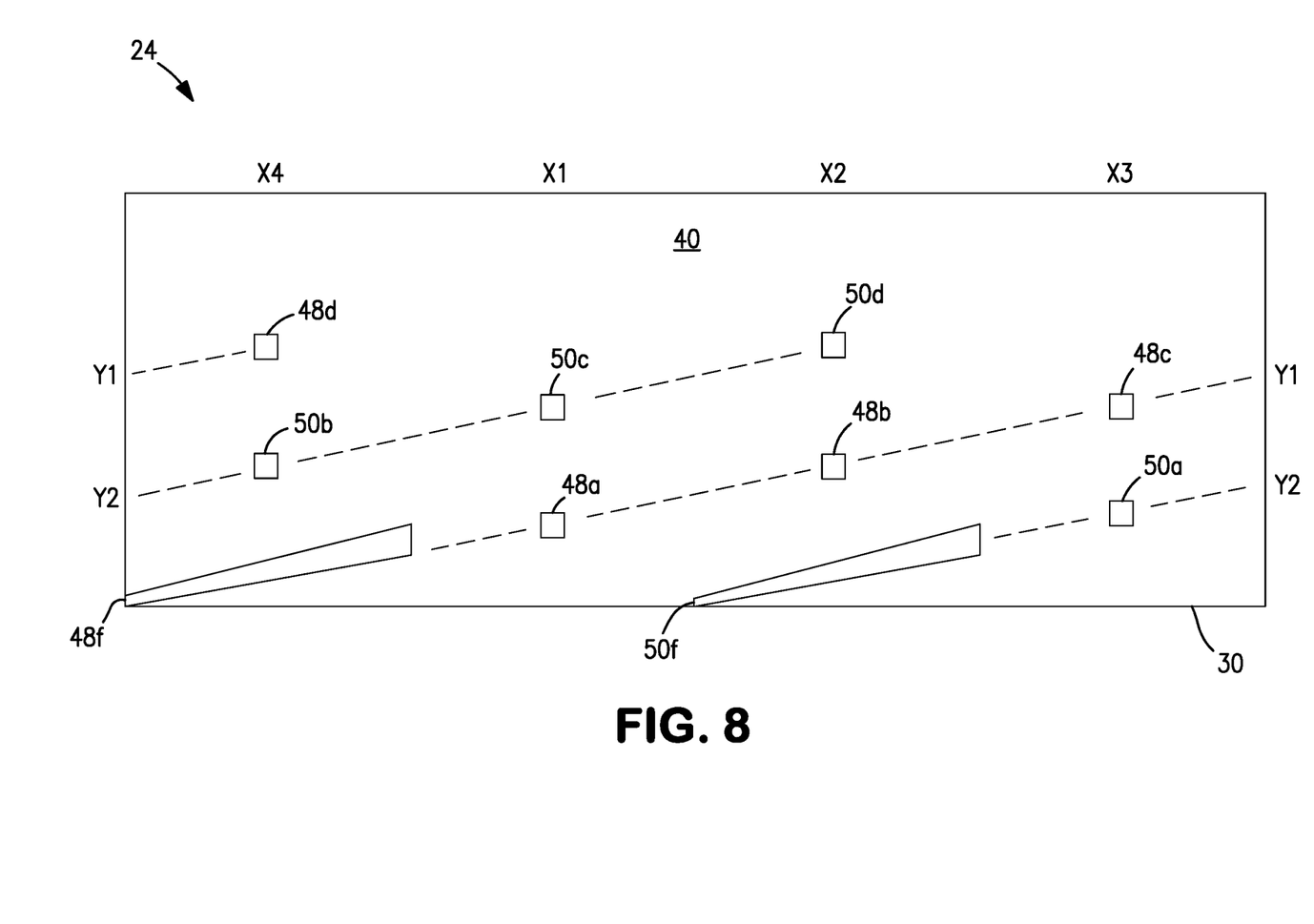
FIG. 8 is a conceptualized two-dimensional projection of the cannula coupling segment which is shown in the cannula of FIG. 1.

With additional reference to FIG. 8, a plurality of coupling projections 48a, 48b, 48c, 48d, 50a, 50b, 50c, 50d are distributed in an array on the substantially cylindrical outer surface 40 of the cannula coupling segment 24. The present array of coupling projections shown and described by way of example herein is a 2×4 array having two helical rows and four vertical columns. Each helical row Y1, Y2 consists of four coupling projections in alignment with one another along a respective helical cannula coupling pathway. The first row Y1 consists of the four coupling projections 48a, 48b, 48c, 48d which are termed first row coupling projections. The second row Y2 consists of the four coupling projections 50a, 50b, 50c, 50d which are termed second row coupling projections. The helical cannula coupling pathway of each row has a relatively gradual incline, i.e., slope <1, giving the row a substantially horizontal orientation.

Each vertical column X1, X2, X3, X4 consists of a pair of coupling projections in vertical alignment with one another. Thus, the first column X1 consists of the two coupling projections 48a, 50c, the second column consists of the two coupling projections 48b, 50d, the third column consists of the two coupling projections 48c, 50a and the fourth column consists of the two coupling projections 48d, 50b. The four columns X1, X2, X3, X4 of paired coupling projections are evenly spaced around the circumference of the outer surface 40 of the cannula coupling segment 24 at 90° intervals.

Each coupling projection is integrally formed with the outer surface 40 of the cannula coupling segment 24 and juts radially outward from the outer surface 40. Each coupling projection is a nubbin having a similar sawtooth-like profile with a slanted leading face 52 termed a cutting face and a straight trailing face 54. Each coupling projection may be dimensionally characterized by its projection height and projection protrusion distance. The projection height is defined as the distance that the coupling projection extends upward essentially parallel to the central longitudinal axis of the cannula hub 14. The projection protrusion distance is defined as the distance that the coupling projection protrudes radially outward from the central longitudinal axis of the cannula hub 14.

The lower coupling projection in each column X1, X2, X3, X4, i.e., coupling projections 48a, 48b, 50a, 50b, respectively, are all preferably identically dimensioned with respect to one another. The upper coupling projection in each column X1, X2, X3, X4, i.e., coupling projections 48c, 48d, 50c, 50d, respectively, are also preferably identically dimensioned with respect to one another. However, the upper coupling projections 48c, 48d, 50c, 50d are preferably dimensioned slightly larger than the lower coupling projections 48a, 48b, 50a, 50b. Thus, the projection height of the upper coupling projections 48c, 48d, 50c, 50d is slightly greater than the projection height of the lower coupling projections 48a, 48b, 50a, 50b and the projection protrusion distance of the upper coupling projections 48c, 48d, 50c, 50d is slightly greater than the projection protrusion distance of the lower coupling projections 48a, 48b, 50a, 50b. In any case, the projection protrusion distance of each and every coupling projection is greater than the radius of the cannula coupling segment 24 which is defined as the distance between the central longitudinal axis of the cannula hub 14 and the outer surface 40 of the cannula coupling segment 24.

In sum, the projection height and projection protrusion distance of each successive coupling projection within a given column X1, X2, X3, X4 preferably slightly increases when progressing upward from one coupling projection to the next in the same column, e.g., successive coupling projection 50c is dimensioned larger than preceding coupling projection 48a in column X1. Similarly, the projection height and projection protrusion distance of the succeeding upper coupling projections preferably slightly increases relative to the preceding lower coupling projections within a given row Y1, Y2 when progressing upwardly along the respective helical cannula coupling pathway of the row, e.g., successive upper coupling projections 48c, 48d are dimensioned larger than preceding lower coupling projections 48a, 48b in row Y1.

The cannula coupling segment 24 additionally includes first and second coupling alignment guides 48e, 50e each of which is a helical ridge jutting radially outward from the outer surface 40 of the cannula coupling segment 24, thereby forming an external thread segment. The coupling alignment guides 48e, 50e are both preferably identically dimensioned with respect to one another. The coupling alignment guides 48e, 50e have first and second start points 48f, 50f, respectively, that are positioned on the outer surface 40 at opposite sides of the base 30 180° apart from one another. Each coupling alignment guide 48e, 50e extends an arc length of about 90° around the outer surface 40 along the respective helical cannula coupling pathway from the base 30 toward its adjacent lower coupling projection 48a, 50a, respectively. The projection protrusion distances of the coupling alignment guides 48e, 50e are equal to one another and are preferably slightly less than the projection protrusion distance of the lower coupling projections 48a, 48b, 50a, 50b.

Figure 9:
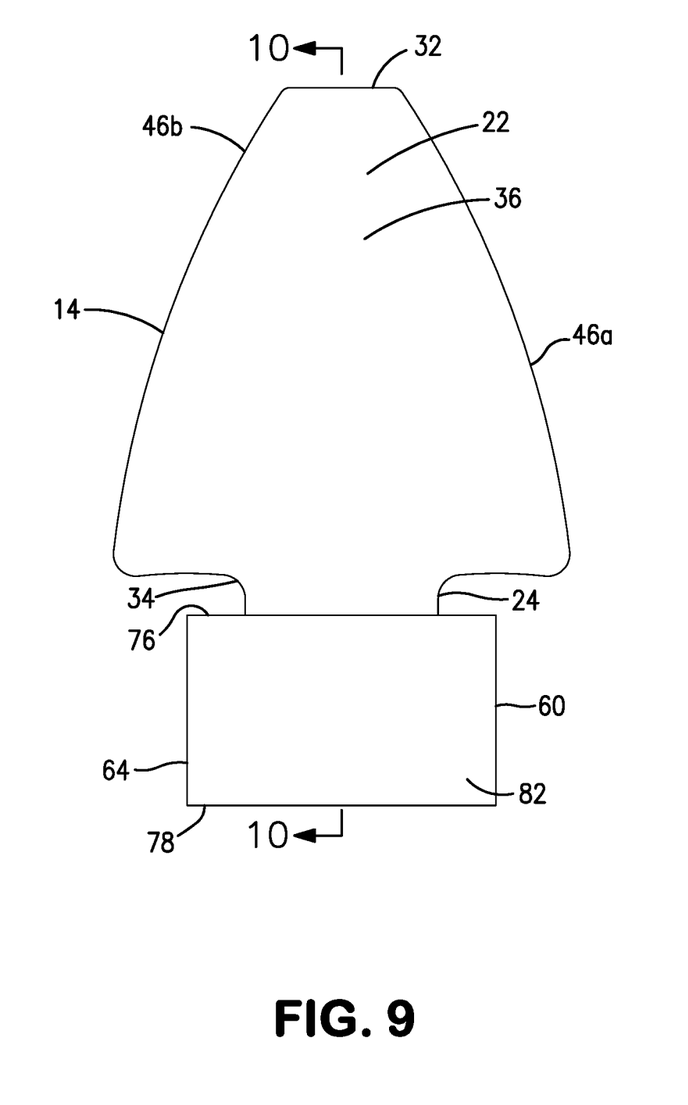
FIG. 9 is a side elevation view of the cannula hub, which is shown in the cannula of FIG. 1, but is coupled with a transfer vessel coupling segment in FIG. 9.
Figure 10:
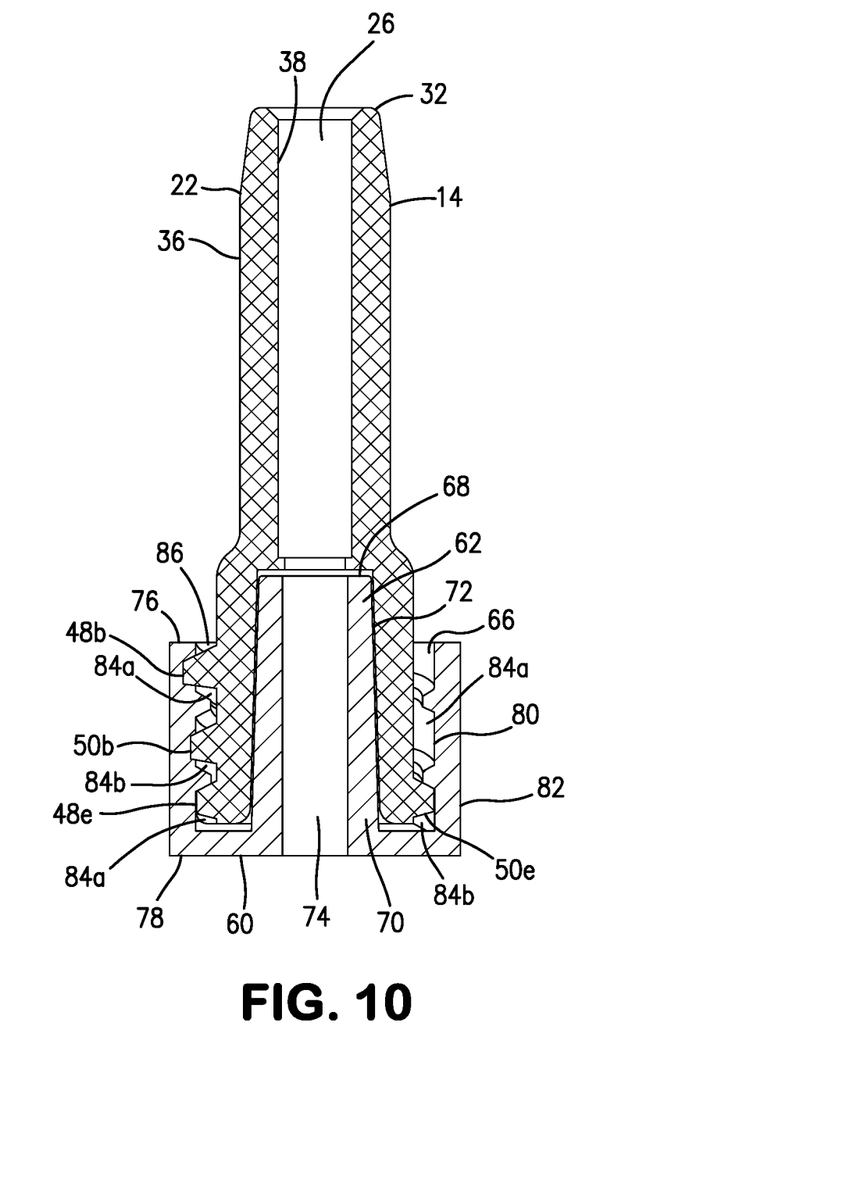
FIG. 10 is a cross section of the cannula hub and transfer vessel coupling segment of FIG. 9 taken along the section line 10-10.

Referring to FIGS. 9 and 10, the cooperative combination of coupling projections 48a, 48b, 48c, 48d, 50a, 50b, 50c, 50d and coupling alignment guides 48e, 50e function as a male coupler enabling secure coupling of the cannula hub 14 with a tip assembly 60 that is integrally formed on the end of a transfer vessel. Although the drawings do not show the remainder of the transfer vessel beyond its tip assembly 60, it is understood that the remainder of the transfer vessel extends away from the tip assembly 60 in a direction opposite the cannula hub 14. A transfer vessel having utility herein may be a syringe of the type shown and described in U.S. patent Ser. No. 10/702,629 or may be some other type of known transfer vessel.

The tip assembly 60 comprises a first tube 62 termed a transfer vessel port and a second tube 64 termed a transfer vessel coupling segment. The transfer vessel port 62 and transfer vessel coupling segment 64 are positioned in coaxial relation to one another with the transfer vessel port 62 nested within the transfer vessel coupling segment 64 and an annular recess 66 formed between them. The transfer vessel port 62 has a first port end 68, an opposing second port end 70 and a port outer surface 72.

The first port end 68 is an open upper end of the transfer vessel port 64 that is enclosed by the cannula coupling segment 24 when the cannula hub 14 is coupled with the tip assembly 60. The second port end 70 is an open lower end of the transfer vessel port 64 that opens into the interior of the transfer vessel (not shown). A longitudinal port bore 74 extends the entire length of the transfer vessel port 62 from the first port end 68 to the second port end 70 and provides communication between the interior of the transfer vessel and the longitudinal hub bore 26. The outer surface 72 of the transfer vessel port 62 has a slight taper as it extends from the second port end 70 to the first port end 68 that corresponds to the taper of the second hub bore segment 28.

The transfer vessel coupling segment 64 has a first or upper end 76, an opposing second or lower end 78, an inner surface 80 and an exposed outer surface 82. The inner surface 80 is configured as a female coupler that is more specifically termed a female Luer connector. The inner surface 80 has first and second grooves 84a, 84b formed therein that face the annular recess 66 and the adjacent outer surface 72 of the transfer vessel port 62. Both grooves 84a, 84b are preferably identically dimensioned with respect to one another. Each of the grooves 84a, 84b functions as an internal thread and, as such, preferably has a constant groove depth and groove height. The groove depth is defined as the distance between the inside face of the groove and the central longitudinal axis of the cannula hub 14. The groove height is defined as the distance from the bottom edge to the top edge of the groove. The grooves 84a, 84b have respective start points that are positioned on the inner surface 80 at opposite sides of the upper end 76 of the transfer vessel coupling segment 64 180° apart from one another. Only the start point 86 of the first internal thread 84a is shown in FIG. 10. The start point of the second internal thread 84b has been cut away in the cross section view of FIG. 10 and is not shown.

Secure coupling of the cannula hub 14 and transfer vessel by means of the cannula coupling segment 24 and cooperative transfer vessel coupling segment 64 permits material to be received into the transfer vessel or material to be discharged from the transfer vessel via the serially positioned cannula shaft 12, cannula hub 14 and transfer vessel port 62. Secure coupling is typically effected by a medical practitioner immediately prior to performing a desired medical procedure.

The medical practitioner initiates coupling by positioning the cannula coupling segment 24 atop the transfer vessel coupling segment 64. The practitioner grasps the wings 46a, 46b on the shaft mount segment 22 and rotates the cannula hub 14 clockwise and downward, thereby pushing the cannula coupling segment 24 into the annular recess 66 of the tip assembly 60 such that the start points 48f, 50f of the coupling alignment guides 48e, 50e, respectively, engage the start points of the grooves 84a, 84b, respectively. The coupling alignment guides 48e, 50e and grooves 84a, 84b are preferably correspondingly dimensioned so that the coupling alignment guides 48e, 50e are cooperatively rotationally received with ease within the grooves 84a, 84b, respectively, in the manner of a nut and bolt. Rotating the cannula hub 14 clockwise and downward also causes the first end 68 of the transfer vessel port 62 to extend upward into the second hub bore segment 28 via the base 30 corresponding to the open bottom end 30 of the cannula coupling segment 24.

The practitioner continues clockwise downward rotation of the cannula hub 14, thereby extending the transfer vessel port 62 further up into the second hub bore segment 28, extending the cannula coupling segment 24 further down into the annular recess 66 and advancing the coupling alignment guides 48e, 50e further along the helical downward path of the grooves 84a, 84b, respectively, until the cutting faces 52 on the lower coupling projections 48a, 50a engage the start points of the grooves 84a, 84b, respectively.

In order to still further advance the cannula coupling segment 24 down into the annular recess 66, the lower coupling projections 48a, 50a must be advanced along the helical path of the grooves 84a, 84b, respectively. However, the projection height and projection protrusion distance of the lower coupling projections 48a, 50a, 48b, 50b is slightly greater than the groove height and groove depth of the grooves 84a, 84b, thereby resisting advancement of the lower coupling projections 48a, 50a along the grooves 84a, 84b, respectively. Therefore, the practitioner must supply sufficient clockwise downward rotational force to the cannula hub 14 to cause the cutting faces 52 of the lower coupling projections 48a, 50a to score the inside face and top and bottom edges of the groove, thereby increasing the groove height and groove depth of the grooves 84a, 84b in correspondence with the projection height and projection protrusion distance of the lower coupling projections 48a, 50a. The grooves 84a, 84b are resized to a first expansion size in the manner described above, thereby enabling the lower coupling projections 48a, 50a and following lower coupling projections 48b, 50b to advance along the grooves 84a, 84b, respectively, although advancement still requires substantial effort due to the tight compression fit of the lower coupling projections 48a, 50a, 48b, 50b in the first resized grooves 84a, 84b.

The practitioner continues clockwise downward rotation of the cannula hub 14 still further, thereby advancing the lower coupling projections 48a, 50a, 48b, 50b further along the first resized grooves 84a, 84b until the cutting faces 52 on the upper coupling projections 48c, 50c engage the start points of the first resized grooves 84a, 84b, respectively. The projection height and projection protrusion distance of the upper coupling projections 48c, 50c, 48d, 50d is slightly greater than the groove height and groove depth of the first resized grooves 84a, 84b, thereby resisting advancement of the upper coupling projections 48c, 50c along the first resized grooves 84a, 84b, respectively. Therefore, the practitioner must supply sufficient clockwise downward rotational force to the cannula hub 14 to cause the cutting faces 52 of the upper coupling projections 48c, 50c to re-score the inside face and top and bottom edges of the groove, thereby increasing the groove height and groove depth of the first resized grooves 84a, 84b in correspondence with the projection height and projection protrusion distance of the upper coupling projections 48c, 50c.

The first resized grooves 84a, 84b are again resized to a second expansion size in the manner described above, thereby enabling the upper coupling projections 48c, 50c and following upper coupling projections 48d, 50d to advance along the grooves 84a, 84b, respectively, although advancement still requires substantial effort due to the tight compression fit of the upper coupling projections 48c, 50c, 48d, 50d in the second resized grooves 84a, 84b.

Secure coupling of the cannula hub 14 and transfer vessel is completed when all of the coupling projections 48a, 48b, 48c, 48d and 50a, 50b, 50c, 50d are received into the first and second grooves 84a, 84b, respectively, via the base 30 corresponding to the open bottom end of the cannula coupling segment 24, the start points 48f, 50f of the coupling alignment guides 48e, 50e jutting therefrom reach the bottom of the annular recess 66 and the first end 68 of the transfer vessel port 62 reaches the intersection 34 at the top of the second hub bore segment 28.

It is apparent that the present configuration of the cannula hub 14 provides an effective secure coupling between the cannula hub 14 and transfer vessel because the first coupling alignment guide 48e and first row coupling projections 48a, 48b, 48c, 48d are aligned along a first helical cannula coupling pathway that emulates a first external thread and the second coupling alignment guide 50e and second row coupling projections 50a, 50b, 50c, 50d are aligned along a second helical cannula coupling pathway that emulates a second external thread. The first coupling alignment guide 48e and first row coupling projections 48a, 48b, 48c, 48d are serially receivable within a first groove of a transfer vessel that functions as a first internal thread and the second coupling alignment guide 50e and second row coupling projections 50a, 50b, 50c, 50d are receivable within a second groove of the transfer vessel that functions as a second internal thread.

All of the coupling projections are dimensioned larger than the grooves in the tip assembly of the transfer vessel in which the coupling projections are received. Furthermore, at least one succeeding coupling projection is dimensioned larger than at least one of its preceding coupling projections that is received in a respective groove of the tip assembly before the succeeding coupling projection. Thus, for example, the succeeding coupling projection 48c and/or 48d that is received in the first groove 84a after the preceding coupling projection 48a and/or 48b is dimensioned larger the preceding coupling projection 48a and/or 48b. The succeeding coupling projection 50c and/or 50d that is received in the second groove 84b after the preceding coupling projection 50a and/or 50b is also preferably dimensioned larger than preceding coupling projection 50a and/or 50b. As a result, each degree of clockwise rotation of the cannula hub 14 cuts further into each groove 84a, 84b of the tip assembly 60, thereby deepening and heightening the groove 84a, 84b. The resulting tight compression fit of the coupling projections of the cannula coupling segment 24 in the deepened and heightened grooves 84a, 84b of the tip assembly 60 more firmly secures the coupling between the cannula hub and transfer vessel and resists forces applied to the coupling during use that could otherwise undesirably loosen or self-release the coupling.

It is understood that alternatives and modifications to the above-described cannula hub, such as those suggested herein and others in the purview of the ordinary artisan, fall within the scope of the present invention. For example, although the embodiment of the cannula hub described above is specifically configured to couple a syringe needle with a syringe barrel and plunger assembly, it is understood that this same cannula hub as presently configured, or with minor structural modification(s) readily apparent to the ordinary artisan, can be used to couple alternate cannulas to syringe barrel and plunger assemblies or to couple cannulas to other types of transfer vessels such as hoses or tubes in communication with storage or supply reservoirs.

It is further understood that although the embodiment of the cannula hub described above has a specific number of coupling projections in a specific array included thereon, it is within the purview of one of ordinary skill in the art depending on the particular needs of the specific medical application for which the cannula hub is employed to provide the cannula hub with an alternate number of coupling projections and/or in an alternate array. As such, the present invention is not limited to any specific number of coupling projections or specific array on the cannula hub.

The cannula described herein is a single-use disposable device. However, a cannula having essentially the same configuration can alternatively be constructed for multi-use with sterilization between each use by fabricating both the shaft and hub as an integral unit from a durable sterilizable metal such as stainless steel.

I claim:

1. A cannula hub comprising:
   a cannula coupling segment having a tubular configuration with a base and an outer surface; and
   a set of coupling nubbins radially extending from said outer surface, wherein said set includes a first coupling nubbin and a second coupling nubbin aligned with, but spaced apart from one another along a helical cannula coupling pathway on said outer surface, said first and second coupling nubbins of said set are constructed from a hard rigid material and are adapted to be received within a cooperative first helical groove on a transfer vessel, the first helical groove has a first groove height and a first groove depth, said first coupling nubbin of said set has a cutting face, a protrusion height and a protrusion projection distance, said protrusion height is greater than the first groove height and/or said protrusion projection distance is greater than the first groove depth, such that said cutting face of said first coupling nubbin of said set is adapted to score the first helical groove when said first coupling nubbin of said set is received within the first helical groove, thereby re-sizing the first helical groove to a first expansion size having a first expansion height greater than the first groove height and/or a first expansion depth greater than the first groove depth and said second coupling nubbin of said set has a cutting face, a protrusion height and a protrusion projection distance, said protrusion height of said second coupling nubbin of said set is greater than the first expansion height of the first helical groove and/or said protrusion projection distance of said second coupling nubbin of said set is greater than the first expansion depth of the first helical groove, such that said second coupling nubbin of said set is adapted to be received within the first helical groove after said first coupling nubbin of said set is received therein and to score the first helical groove, thereby re-sizing the first helical groove to a second expansion size having a second expansion height greater than the first expansion height and/or a second expansion depth greater than the first expansion depth.

2. The cannula hub of claim 1, wherein said first coupling nubbin of said set is positioned more proximal to said base along said helical cannula coupling pathway than said second coupling nubbin of said set.

3. The cannula hub of claim 1 further comprising a helical coupling alignment guide radially extending from said outer surface and following said helical cannula coupling pathway around said outer surface.

4. The cannula hub of claim 3, wherein said helical coupling alignment guide has a start point positioned more proximal to said base along said helical cannula coupling pathway than said first and second coupling nubbins of said set.

5. The cannula hub of claim 3, wherein said helical coupling alignment guide has an arc length of about 90°.

6. The cannula hub of claim 3, wherein said helical coupling alignment guide has a protrusion projection distance less than said protrusion projection distance of said first coupling nubbin of said set.

7. The cannula hub of claim 1, wherein said set of coupling nubbins further includes a third coupling nubbin and a fourth coupling nubbin constructed from a hard rigid material and aligned with said first and second coupling nubbins of said set along said helical cannula coupling pathway, said third coupling nubbin of said set is positioned between said first and second coupling nubbins of said set and said fourth coupling nubbin of said set is positioned after said second coupling nubbin of said set on said helical cannula coupling pathway such that each successive coupling nubbin of said set on said helical cannula coupling pathway is separated from its immediately preceding coupling nubbin of said set on said helical cannula coupling pathway by a separation distance.

8. The cannula hub of claim 7, wherein said separation distance has an arc length of about 90° on said helical cannula coupling pathway.

9. The cannula hub of claim 7, wherein said third coupling nubbin of said set has a projection protrusion distance equal to said projection protrusion distance of said first coupling nubbin of said set.

10. The cannula hub of claim 7, wherein said fourth coupling nubbin of said set has a projection protrusion distance equal to said projection protrusion distance of said second coupling nubbin of said set.

11. The cannula hub of claim 7, wherein said third coupling nubbin of said set has a projection protrusion distance equal to said projection protrusion distance of said first coupling nubbin of said set and said fourth coupling nubbin of said set has a projection protrusion distance equal to said projection protrusion distance of said second coupling nubbin of said set.

12. The cannula hub of claim 1, wherein said helical cannula coupling pathway on said outer surface is a first helical cannula coupling pathway and said set of coupling nubbins is a first set of coupling nubbins, said cannula hub further comprising a second set of coupling nubbins including a first coupling nubbin and a second coupling nubbin, wherein said first and second coupling nubbins of said second set are aligned with, but are spaced apart from one another along a second helical cannula coupling pathway on said outer surface, wherein said first and second coupling nubbins are of said second set are adapted to be received within a cooperative second helical groove with a second groove depth on the transfer vessel, and wherein said first coupling nubbin of said second set has a protrusion projection distance that is greater than the second groove depth and said second coupling nubbin of said second set has a protrusion projection distance that is greater than said protrusion projection distance of said first coupling nubbin of said second set.

13. A cannula hub comprising:
a cannula coupling segment having a tubular configuration with a base and an outer surface;
a first set of coupling nubbins radially extending from said outer surface, wherein said first set includes a first coupling nubbin and a second coupling nubbin aligned with, but spaced apart from one another along a first helical cannula coupling pathway on said outer surface, said first and second coupling nubbins of said first set are constructed from a hard rigid material and are adapted to be received within a cooperative first helical groove on a transfer vessel, the first helical groove has a first groove height and a first groove depth, said first coupling nubbin of said first set has a cutting face, a protrusion height and a protrusion projection distance, said protrusion height is greater than the first groove height and/or said protrusion projection distance is greater than the first groove depth, such that said cutting face of said first coupling nubbin of said first set is adapted to score the first helical groove when said first coupling nubbin of said first set is received within the first helical groove, thereby re-sizing the first helical groove to a first expansion size having a first expansion height greater than the first groove height and/or a first expansion depth greater than the first groove depth and said second coupling nubbin of said first set has a cutting face, a protrusion height and a protrusion projection distance, said protrusion height of said second coupling nubbin of said first set is greater than the first expansion height of the first helical groove and/or said protrusion projection distance of said second coupling nubbin of said first set is greater than the first expansion depth of the first helical groove, such that said second coupling nubbin of said first set is adapted to be received within the first helical groove after said first coupling nubbin of said first set is received therein and to score the first helical groove, thereby re-sizing the first helical groove to a second expansion size having a second expansion height greater than the first expansion height and/or a second expansion depth greater than the first expansion depth; and a second set of coupling nubbins radially extending from said outer surface, wherein said second set includes a first coupling nubbin and a second coupling nubbin aligned with, but spaced apart from one another along a second helical cannula coupling pathway on said outer surface, said first and second coupling nubbins of said second set are constructed from a hard rigid material and are adapted to be received within a cooperative second helical groove on the transfer vessel, the second helical groove has a second groove height and a second groove depth, said first coupling nubbin of said second set has a cutting face, a protrusion height and a protrusion projection distance, said protrusion height of said first coupling nubbin of said second set is greater than the second groove height and/or said protrusion projection distance of said first coupling nubbin of said second set is greater than the second groove depth, such that said first coupling nubbin of said second set is adapted to score the second helical groove when said first coupling nubbin of said second set is received within the second helical groove, thereby re-sizing the second helical groove to a first expansion size having a first expansion height greater than the second groove height and/or a first expansion depth greater than the second groove depth and said second coupling nubbin of said second set has a cutting face, a protrusion height and a protrusion projection distance, said protrusion height of said second coupling nubbin of said second set is greater than the first expansion height of the second helical groove and/or said protrusion projection distance of said second coupling nubbin of said second set is greater than the first expansion depth of the second helical groove, such that said second coupling nubbin of said second set is adapted to be received within the second helical groove after said first coupling nubbin of said second set is received therein and to score the second helical groove, thereby re-sizing the second helical groove to a second expansion size having a second expansion height greater than the first expansion height of the second helical groove and/or a second expansion depth greater than the first expansion depth of the second helical groove.

14. The cannula hub of claim 13, wherein said protrusion projection distance of said first coupling nubbin of said first set is equal to said protrusion projection distance of said first coupling nubbin of said second set, said protrusion projection distance of said second coupling nubbin of said first set is equal to said protrusion projection distance of said second coupling nubbin of said second set and the first groove depth is equal to the second groove depth.

15. The cannula hub of claim 13 further comprising a first helical coupling alignment guide radially extending from said outer surface and following said first helical cannula coupling pathway around said outer surface and a second helical coupling alignment guide radially extending from said outer surface and following said second helical cannula coupling pathway around said outer surface.

16. The cannula hub of claim 15, wherein said first helical coupling alignment guide has a first start point positioned more proximal to said base along said first helical cannula coupling pathway than said first coupling nubbin and second coupling nubbin of said first set and said second helical coupling alignment guide has a second start point positioned more proximal to said base along said helical cannula coupling pathway than said first coupling nubbin and second coupling nubbin of said second set.

17. The cannula hub of claim 16, wherein said first start point and said second start point are positioned on said outer surface at opposite sides of said base 180° apart from one another.

18. The cannula hub of claim 15, wherein said first and second helical coupling alignment guide each has an arc length of about 90°.

* * * * *